(12) United States Patent
Buchbinder et al.

(10) Patent No.: US 8,372,097 B2
(45) Date of Patent: *Feb. 12, 2013

(54) VALVULOTOME

(75) Inventors: Dale Buchbinder, Baltimore, MD (US); Paul Koven, St. Louis, MO (US); Joan Koven, legal representative, St. Louis, MO (US)

(73) Assignee: Koven Technology Canada Inc., Manitoba (CA)

( * ) Notice: Subject to any disclaimer, the term of this patent is extended or adjusted under 35 U.S.C. 154(b) by 1032 days.

This patent is subject to a terminal disclaimer.

(21) Appl. No.: 11/734,037

(22) Filed: Apr. 11, 2007

(65) Prior Publication Data

US 2008/0255595 A1    Oct. 16, 2008

Related U.S. Application Data

(63) Continuation-in-part of application No. 11/071,973, filed on Mar. 4, 2005, now abandoned.

(51) Int. Cl.
*A61B 17/32* (2006.01)
(52) U.S. Cl. ...................................................... 606/159
(58) Field of Classification Search .................. 606/159, 606/170, 1, 108, 113, 127, 139, 142, 167, 606/180, 184, 205; 604/22; 81/489; 74/29, 74/32, 33
See application file for complete search history.

(56) References Cited

U.S. PATENT DOCUMENTS

| | | | |
|---|---|---|---|
| 3,557,794 A * | 1/1971 | Van Patten | 606/198 |
| 4,397,091 A * | 8/1983 | Gustavsson et al. | 33/732 |
| 4,493,321 A | 1/1985 | Leather | |
| 5,152,771 A * | 10/1992 | Sabbaghian et al. | 606/159 |
| 5,304,189 A | 4/1994 | Goldberg et al. | |
| 5,658,301 A * | 8/1997 | Lemaitre et al. | 606/159 |
| 5,725,536 A * | 3/1998 | Oberlin et al. | 606/139 |
| 5,902,313 A | 5/1999 | Redha | |
| 6,333,397 B1 | 12/2001 | Katus et al. | |
| 6,514,261 B1 * | 2/2003 | Randall et al. | 606/108 |
| 6,585,694 B1 * | 7/2003 | Smith et al. | 604/181 |
| 2005/0060016 A1 * | 3/2005 | Wu et al. | 623/1.11 |
| 2005/0192606 A1 | 9/2005 | Paul, Jr. et al. | |
| 2005/0209617 A1 | 9/2005 | Koven et al. | |
| 2005/0222568 A1 * | 10/2005 | O'Sullivan et al. | 606/47 |

OTHER PUBLICATIONS

Office Action Summary for U.S. Appl. No. 11/071,973, dated Feb. 21, 2008, 20 pages.
Expandable LeMaitre Valvulotome operational manual, distributed by LeMaitre Vascular, Inc., Copyright 2002 (3 pages).
International Search Report and Written Opinion, International Application No. PCT/US08/57985, dated Aug. 29, 2008 (11 pages).

* cited by examiner

*Primary Examiner* — Gary Jackson
*Assistant Examiner* — Jonathan Hollm
(74) *Attorney, Agent, or Firm* — Polsinelli Shughart PC (57) ABSTRACT

A valvulotome device for cutting valves inside a lumen of a vein having a deployable assembly with deployable cutting blades and guide fins which permit continual centralizing, self-alignment of the cutting blades within the lumen of the vein as the valves are being excised is disclosed. The valvulotome device further includes a handle operatively associated with the deployable assembly through a catheter by the handle in a one-handed operation for deploying the guide fins and cutting blades of the deployable assembly having respective outer diameters at each deployment position.

12 Claims, 9 Drawing Sheets

VALVULOTOME

CROSS REFERENCE TO RELATED APPLICATIONS

This application claims priority from and is a continuation-in part to U.S. patent application Ser. No. 11/071,973 filed on Mar. 4, 2005 now abandoned.

FIELD

This document relates to a medical device for the treatment of vascular disorders, and more particularly to a valvulotome device and related method for excising venous valves when performing in-situ vascular procedures, such as arterial bypass surgery.

SUMMARY

In an embodiment, the valvulotome device may include a handle having a thumb wheel, the thumb wheel being operatively associated with a catheter that encloses a catheter wire, and a deployable assembly operatively engaged to the thumb wheel through the catheter, the deployable assembly including a blade assembly having a plurality of cutting blades and a guide fin assembly having a plurality of guide fins; wherein the deployable assembly is deployable from a closed position to one or more deployment positions upon actuation of the catheter by the thumb wheel such that the blade assembly and the guide fin assembly incrementally and simultaneously deploy to the one or more deployment positions by incremental deployment of the plurality of cutting blades and plurality of guide fins to a respective outer diameter for each of the one or more deployment positions.

In another embodiment, the valvulotome device may include a handle having a thumb wheel, the handle being operatively associated with a catheter wire; a catheter defining a lumen adapted to enclose the catheter wire and in communication with a catheter sheath; and a deployable assembly operatively engaged to the thumb wheel through the catheter, the deployable assembly including a blade assembly having a plurality of deployable cutting blades and a guide fin assembly having a plurality of expandable guide fins, the deployable assembly further including a hollow bullet operatively engaged to the catheter sheath such that the deployable assembly is fully disposed within the bullet and the catheter sheath when the deployable assembly is in a closed position; wherein the deployable assembly is deployable to one or more deployment positions from the closed position upon actuation of the catheter by a one-handed operation of the thumb wheel such that the catheter sheath becomes disengaged or engaged relative to the bullet upon the one-handed operation of the thumb wheel.

In one embodiment, a method of excising venous valves may include providing a valvulotome device having a handle, the handle being operatively associated with a catheter through a thumb wheel; the catheter defining a lumen adapted to enclose a catheter wire and including a catheter sheath; and a deployable assembly operatively engaged to the thumb wheel through the catheter, the deployable assembly including a blade assembly having a plurality of deployable cutting blades and a guide fin assembly having a plurality of expandable guide fins, the deployable assembly further including a hollow bullet operatively engaged to the catheter sheath such that the deployable assembly is fully disposed within the bullet and the catheter sheath when the deployable assembly is in a closed position with the bullet engaged to the catheter sheath; wherein the deployable assembly is deployable to one or more deployment positions upon actuation of the catheter by the thumb wheel; inserting the deployable assembly within the lumen of a vein and extending the deployable assembly through at least one or more valves of the vein; rotating the thumb wheel such that the catheter sheath disengages from the bullet and the deployable assembly assumes one of the one or more deployment positions by simultaneous deployment of the blade assembly and the guide fin assembly by the deployable assembly from the closed position, each of the one or more deployment positions attained by the deployable assembly causing the plurality of cutting blades and the plurality of guide fins to attain a respective outer diameter; and withdrawing the deployable assembly back through the lumen of the vein such that guide fin assembly and the cutting blade assembly is in a particular deployment position when the cutting blade assembly excises the valves of the vein.

Implementation of the above embodiments may include one or more of the following features:

The respective outer diameter of the guide fins is larger than the respective outer diameter of the cutting blades at each of the one or more deployment positions.

The guide fins and the cutting blades have no outer diameter in said closed position.

The handle includes a first casing engaged to a second casing, the first casing and the second casing collectively defining a chamber in communication with a slot and an opening.

The thumb wheel is rotatable disposed within the slot.

The valvulotome device further includes a strain relief engaged to the opening of the handle, the strain relief having a neck defining an aperture adapted to permit the catheter to be inserted therethrough.

The catheter defines a proximal end operatively associated with the thumb wheel and a distal end that communicates with a hollow catheter sheath, the catheter sheath being engaged to a hollow bullet for collectively containing the deployable assembly in the closed position.

The hollow catheter sheath becomes disengaged from the hollow bullet when the deployable assembly deploys to one or more deployment positions.

The hollow catheter sheath becomes disengaged or engaged to the hollow bullet when the catheter is actuated by the handle.

The hollow catheter sheath becomes engaged to the hollow bullet when the catheter moved away from the handle, while the catheter sheath becomes disengaged from the hollow bullet when the catheter is moved toward said handle.

The slot defines a pointed indicator and the thumb wheel includes a visual indicator having a series of numbers corresponding to the outer diameter for a particular deployment position taken by the guide fin assembly, wherein the pointed indicator points to one of the series of numbers to indicate the particular deployment position of the deployable assembly.

Each of the plurality of guide fins includes a long portion and a short portion with a bendable portion interposed between the long portion and the short portion for permitting each of the plurality of guide fins to expand to the one or more deployment positions.

Each of the plurality of guide fins has the same outer diameter and each of the plurality of cutting blades has the same outer diameter.

The catheter wire maintains a fixed spatial relationship between the handle and the deployable assembly.

The first casing and the second casing collectively define a track, the first casing defining a pair of arcuate tracks.

The handle further includes a linear rack, the linear rack being adapted for linear movement along the track, the linear rack defining a first rack body and a second rack body that collectively define a channel and an anchor portion adapted to engage the catheter, the first rack body defining a plurality of rack gear teeth.

The catheter includes a flange adapted to be disposed inside the anchor portion of the linear rack, wherein linear movement of the linear rack causes movement of the catheter is either a distal or proximal direction such that movement in the distal direction causes the deployable assembly to deploy from the closed position to one or more sequential deployment positions.

The thumb wheel includes a wheel gear and a wheel body, the wheel body defining a rounded peripheral edge having a plurality of openings in communication with a cavity, the wheel gear having a pinion gear portion defining a plurality of pinion gear teeth adapted to engage the rack gear teeth of the linear rack, the wheel gear further including an arm portion defining a pair of opposing teeth, the opposing teeth being adapted to incrementally engage the pair of arcuate tracks when the thumb wheel is rotated.

The first casing defines a set screw base adapted to receive a set screw, the set screw being adapted to engage the catheter wire.

Each of the raised protrusions includes a respective marker, each respective marker providing a visual indication as to the rotational direction of the thumb wheel.

The rotation of the thumb wheel in one direction causes the linear rack to move the catheter in the proximal direction and rotation of the thumb wheel in an opposite direction causes the liner track to move the catheter in the distal direction.

The guide fin assembly is interposed between the cutting assembly and the handle.

The guide fin assembly is interposed between the cutting assembly and the handle.

The one-handed operation of the thumb wheel causes the catheter to move in a proximal direction or a distal direction such that movement of the catheter in the proximal direction causes the deployable assembly to move from the closed position to one or more deployment positions while movement of the catheter in the distal direction causes the deployable assembly to move from the one or more deployment positions to the closed position.

The one-handed operation of the thumb wheel in one direction causes the catheter to move in a proximal direction such that the catheter sheath moves away and disengages the bullet while the one-handed operation of the thumb wheel in an opposite direction causes the catheter to move in the distal direction such that the catheter sheath moves towards the bullet.

The method further comprising rotating the thumb wheel in an opposite direction such that the catheter sheath moves toward the bullet.

The outer diameter of the plurality of guide fins is larger than the outer diameter of the plurality of cutting blades at any of the one or more deployment positions by the deployable assembly.

Withdrawing the deployable assembly back through the lumen of the vein allows for closure of the valve around the connection tube prior to being excised by the cutting blades.

Additional objectives, advantages and novel features will be set forth in the description which follows or will become apparent to those skilled in the art upon examination of the drawings and detailed description which follows

BRIEF DESCRIPTION OF THE DRAWINGS

FIGS. 17-21 are perspective views that illustrate a sequence of deploying the deployable assembly by the handle; and FIGS. 17A-21A are end views that correspond to FIGS. 17-21 that illustrate the same sequence of deploying the deployable assembly by the handle.

Corresponding reference characters indicate corresponding elements among the view of the drawings. The headings used in the figures should not be interpreted to limit the scope of the claims.

DETAILED DESCRIPTION

Figure 1:
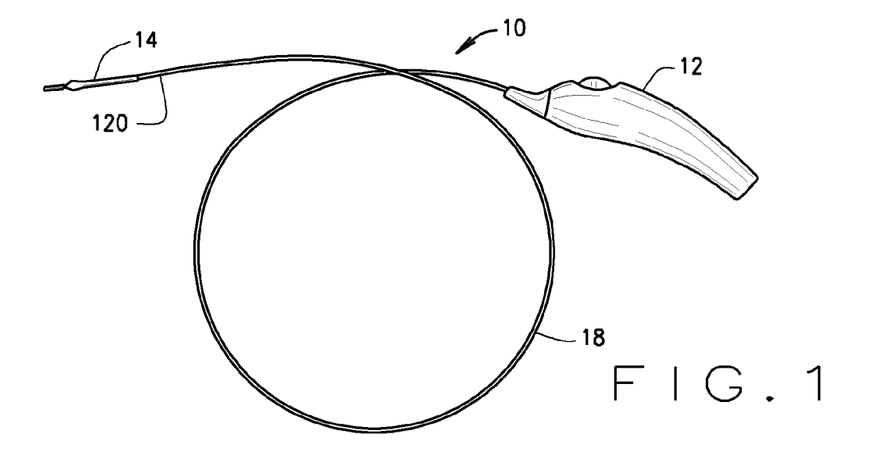
FIG. 1 is a side view of the valvulotome device showing a handle operatively engaged to a deployable assembly.
Figures 2, 3:
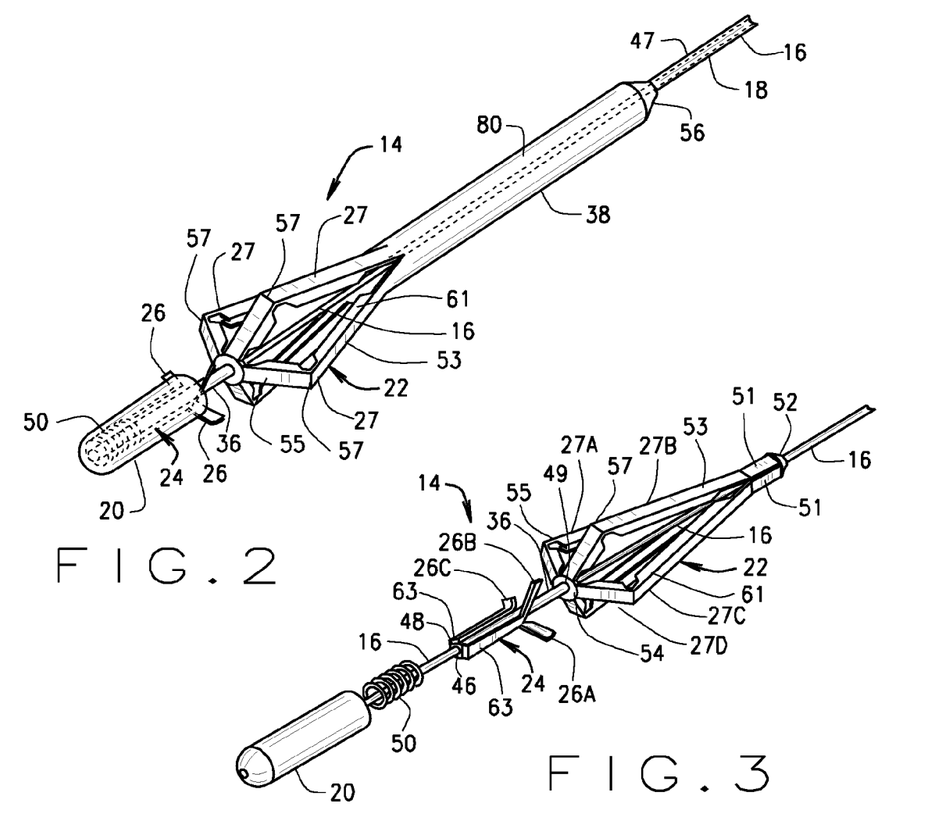
FIG. 2 is a perspective view of the deployable assembly.
FIG. 3 is an exploded view of the deployable assembly without the catheter and catheter sheath.

Referring to the drawings, an embodiment of the valvulotome device is illustrated and generally indicated as 10 in FIG. 1. The valvulotome device 10 provides a means for cutting or excising the valves inside a lumen of a patient's vein (not shown) using a single-handed operation of the valvulotome device 10. In addition, the valvulotome device 10 permits a continual and centralizing, self-alignment of the valvulotome device 10 within the vein that maintains an open vein lumen as the valvulotome device 10 is being withdrawn through the vein after insertion. As shown in FIGS. 1 and 2, the valvulotome device 10 may include a handle 12 operatively engaged to a deployable assembly 14 through a catheter 18 that defines a lumen 47 that encloses a catheter wire 16. Operation of the handle 12 by the user actuates the deployable assembly 14 to one or more incremental deployment positions after the deployable assembly 14 has been inserted into the lumen of the vein and past at least one valve within the vein as shall be discussed in greater detail below. As used herein, the term "proximal" shall mean the direction towards to the handle 12, while the term "distal" shall mean the direction away from the handle 12.

Figure 4:
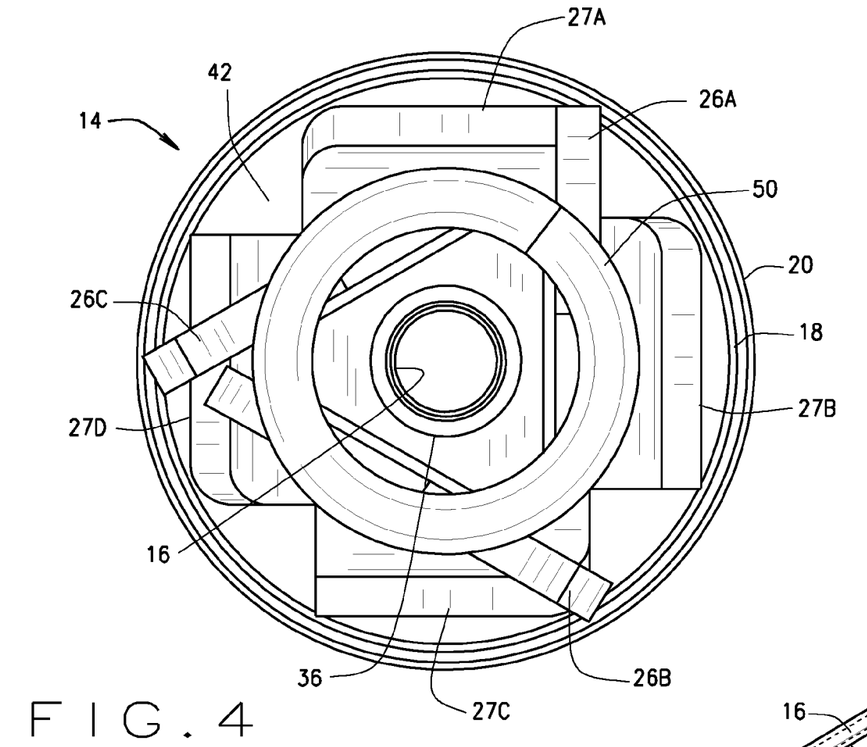
FIG. 4 is an end view of the deployable assembly.

Referring to FIGS. 2-4, the deployable assembly 14 may include a blade assembly 24 having a plurality of deployable cutting blades 26 spaced equidistantly about the blade assembly 24 with the cutting blades 26 being adapted for cutting or excising one or more valves inside the lumen of a vein during deployment and operation of the deployable assembly 14 as shall be discussed in greater detail below. In one embodiment, the blade assembly 24 may include three cutting blades 26A-26C spaced equidistantly about the blade assembly 24, although other embodiments may have two or more cutting blades 26 spaced about the blade assembly 24. As shown in FIG. 3, each respective cutting blade 26A-26C may define a distal portion 63 that forms an apex 46 that defines a center hole 48 adapted to receive a hollow connection tube 36 and to allow the catheter wire 16 to pass through the blade assembly 24. The blade assembly 24 may be biased such that the cutting blades 26A-26C are forced incrementally outward from a closed and fully retracted position to one or more unretracted deployment positions for providing a fixed outer diameter by the cutting blades 26 when the deployable assembly 14 assumes a particular deployment position.

In one embodiment, the deployable assembly 14 may further include an expandable guide fin assembly 22 that provides a means for permitting the deployable assembly 14 to establish and maintain a continual and centralizing, self-alignment of the deployable assembly 14 within the lumen of the vein as the deployable assembly 14 is being withdrawn through the vein. In addition, the guide fin assembly 22 provides a means of keeping the lumen of the vessel open ahead of the cutting blades 26 as the deployable assembly 14 is being withdrawn through the vein during operation of the valvulotome device 10, therefore ensuring that the cutting blades 26 do not contact or otherwise cut the vein wall during deployment. The guide fin assembly 22 may include a plurality of expandable guide fins 27 adapted to expand from a fully bent position (e.g. closed position) to one or more deployment positions in order to achieve an outer diameter tailored to the particular size of the vein having valves to be excised by the valvulotome device 10. Further, the outer diameter of the guide fins 27 at any particular deployment position will always be greater than the outer diameter of the cutting blades 26 at that same deployment position in order to prevent contact of the vein wall by the cutting blades 26 as the deployable assembly 14 is being withdrawn through the lumen of the vein as the valves are being excised.

In an embodiment, the guide fin assembly 22 may include four equally spaced expandable guide fins 27A-27D that are adapted to incrementally expand from the closed position to one or more deployment positions having various outer diameters for each particular deployment position when the deployable assembly 14 is actuated by operation of the handle 12. In addition, operation of the handle 12 may also incrementally return the guide fin assembly 22 and the blade assembly 24 to the closed position or other deployment positions if desired. The guide fins 27 may meet to form an apex 54 at one end of the guide fin assembly 22 that collectively define a hole 49 adapted to secure one end of the hollow rigid connection tube 36, while the other end of the connection tube 36 is secured to the apex 46 of the blade assembly 24. As such, the connection tube 36 physically connects the guide fin assembly 22 to the blade assembly 24 in a fixed spatial relationship. The connection tube 36 also allows closure of the valve around the connection tube 36 after the guide fin assembly 22 has passed therethrough but prior to the valve being excised by the cutting blade 26 of blade assembly 24 as the deployable assembly 14 is being withdrawn through the vein. Further, the connection tube 36 defines a conduit (not shown) for insertion of the catheter wire 16 therethrough in order to facilitate actuation of the deployable assembly 14.

Figure 5:
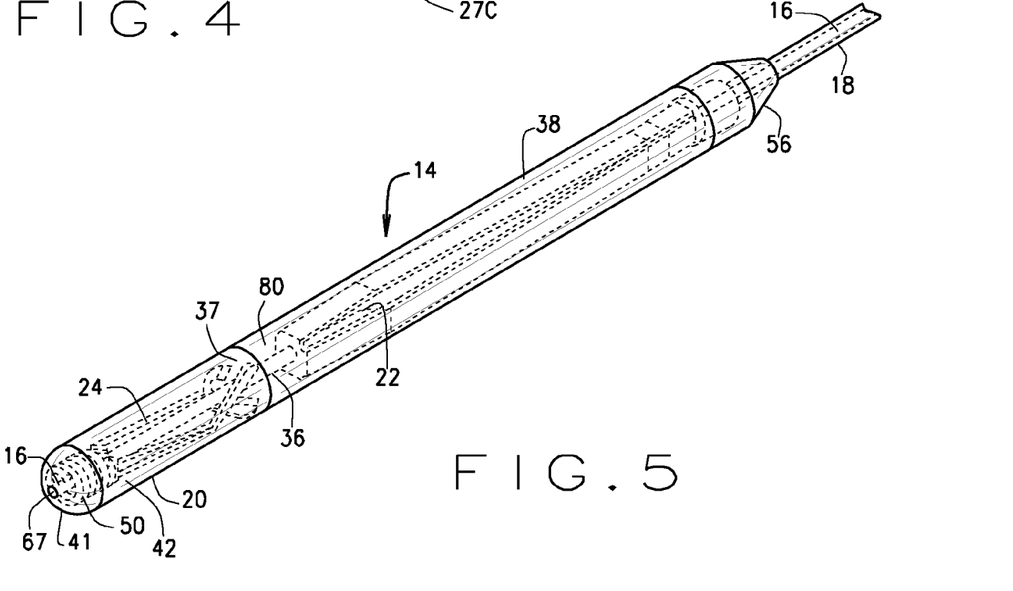
FIG. 5 is a perspective view of the deployable assembly shown in the closed position.

The deployable assembly 14, illustrated in the closed position in FIG. 5, further includes a hollow bullet 20 (shown in phantom) that defines a bullet chamber 42 in communication with a hollow dome portion 41 that encases a part of the deployable assembly 14, while the catheter 18 defines a distal end 120 that includes a tapered portion 56 which communicates with a hollow catheter sheath 38. The catheter sheath 38 defines a sheath chamber 80 that encloses a portion of the deployable assembly 14 including the guide fin assembly 22 when the deployable assembly 14 is in the closed position.

The catheter wire 16 may have an elongated wire body defining a proximal end 65 that anchors the catheter wire 16 to the handle 12 and a distal end 67 that may be soldered or otherwise secured to the dome portion 41 of the bullet 20 such that a fixed spatial relationship may be established between the deployable assembly 14 and the handle 12. This fixed spatial relationship facilitates the engagement or disengagement of the catheter sheath 38 relative to the bullet 20 when actuating the deployable assembly 14. In addition, a compression spring 50 may be operatively engaged to the dome portion 41 of the bullet 20 in order to provide a biasing force during actuation of the deployable assembly 14 by the handle 12.

In the closed position, the cutting blades 26 of the blade assembly 24 are in a fully retracted position and the guide fins 27 of the guide fin assembly 22 are in a fully bent (non-expanded) position such that the guide fin assembly 22 and the blade assembly 24 are fully enclosed by the catheter sheath 38 and the bullet 20. In the one or more deployable positions that may be assumed by the deployable assembly 14 the catheter sheath 38 incrementally disengages and is incrementally spaced away from the bullet 20.

Referring back to FIGS. 2 and 3, each guide fin 27 of guide fin assembly 24 defines a long portion 53 and a short portion 55 with a bendable portion 57 interposed between each portion 53 and 55 that permits the guide fins 27 to be incrementally deployed in various fixed expanded positions during actuation of the deployable assembly 14 to one or more deployment positions. Each long portion 53 and short portion 55 of guide fin 27 defines opposing flanges 61 that terminate proximate each bendable portion 57 in order to facilitate expansion of each guide fin 27 to one or more incrementally fixed expanded positions during deployment. In one embodiment, the guide fin assembly 24 may be constructed of a resilient, bendable metallic material that permits each guide fin 27 to be simultaneously expanded to a number of fixed expanded positions having progressively larger outer diameters at each subsequent incremental deployment position. In addition, each of the plurality of guide fins 27 has the same outer diameter as the guide fins 27 attain progressively larger outer diameters at each subsequent incremental deployment position.

As further shown, each guide fin 27 defines a respective proximal end 51 that is secured to an end block 52. The end block 52 defines a channel (not shown) that is adapted to permit the catheter wire 16 to freely slide through the end block 52 and communicate with connection tube 36.

The catheter sheath 38 defines an opening 37 at one end and the hollow tapered portion 56 at the opposite end thereof that encloses the catheter wire 16 and guide fin assembly 22. The lumen 47 of the elongated catheter 18 is adapted to permit the catheter wire 16 to freely slide through the lumen of the catheter 18 during operation of the valvulotome device 10 in order to maintain the fixed spatial relationship established by the catheter wire 16.

Referring to FIGS. 17-21 and 17A-21A, the sequence for deploying the deployable assembly 14 is illustrated in both perspective and corresponding end views. In the closed position shown in FIGS. 17 and 17A, the bullet 20 is engaged to the opening 37 of the catheter sheath 38 and both the guide fin assembly 22 and the blade assembly 24 of deployable assembly 14 are enclosed by the catheter sheath 38 and bullet 20, respectively. In this closed position, the deployable assembly 14 is inserted through the vein and past at least one valve of the vein. After the deployable assembly 14 has been inserted through the vein, the deployable assembly 14 may be placed from a closed position to four possible incremental deployment positions wherein the guide fin assembly 22 may attain a particular outer diameter by guide fins 27 as the deployable assembly 14 begins to be withdrawn through the vein. However, other embodiments of the valvulotome device 10 may have the deployment assembly 14 assume one or more different deployment positions with the guide fin assembly 22 assuming a different outer diameter for each respective deployment position.

As noted above, the valvulotome device 10 may have four potential deployment positions for the blade assembly 24 and the guide fin assembly 14. In one embodiment, the guide fins 27 of guide fin assembly 22 may deploy having outer diameters of 2.5 mm (FIGS. 18 and 18A), 3.5 mm (FIGS. 19 and 19A) and 4.5 mm (FIGS. 20 and 20A) and 5.5 mm (FIGS. 21 and 21A), respectively, at each respective deployment position. In similar fashion, the blade assembly 24 will concurrently deploy the cutting blades 26 with outer diameters that are less than the outer diameters of the guide fins 27 discussed above at each respective deployment position such that the cutting blades 26 are prevented from contacting the wall of the vein as the deployable assembly 14 is being withdrawn through the vein.

After the deployable assembly 14 has been sufficiently inserted through the vein and once the handle 12 is actuated by rotating the thumb wheel 30 in a one-handed operation by the user, the deployable assembly 14 is placed from the closed position (FIGS. 17 and 17A) to one or more sequential and incremental deployment positions as the catheter sheath 38 becomes detached from the bullet 20 in order to assume the one or more incremental deployment positions illustrated in FIGS. 18-21. As the deployable assembly 14 assumes one or more of the deployment positions the cutting blades 26 all have the same outer diameter as the blade assembly 24 is moved incrementally either outward or inward from one deployment position to another sequential deployment position or even return to the closed position.

In an embodiment, the guide fin assembly 22 and blade assembly 24 are deployed simultaneously as the deployable assembly 14 assumes a particular deployment position. As noted above, the cutting blades 26 and guide fins 27 will have the different outer diameters for each respective deployment position with the guide fins 27 always having a greater outer diameter than the cutting blades 26 at any particular deployment position in order to prevent the cutting blades from contacting the vein wall.

Figure 6:
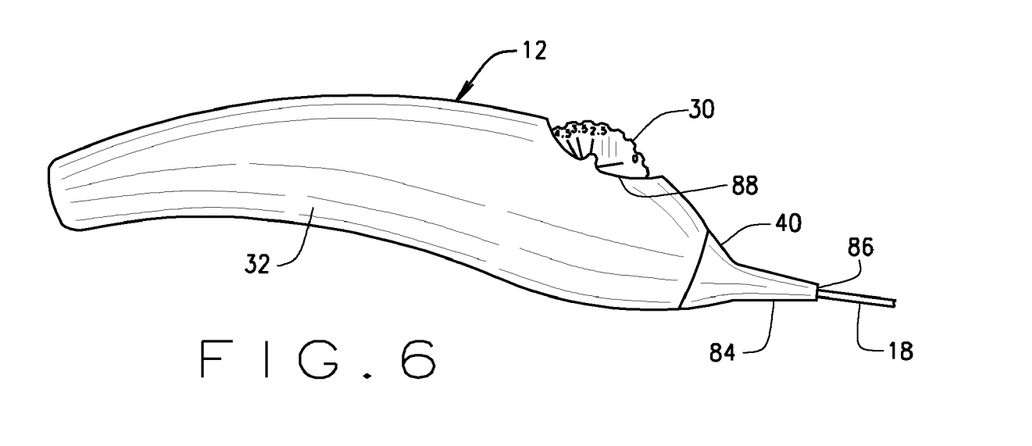
FIG. 6 is a perspective view of the handle.
Figure 7:
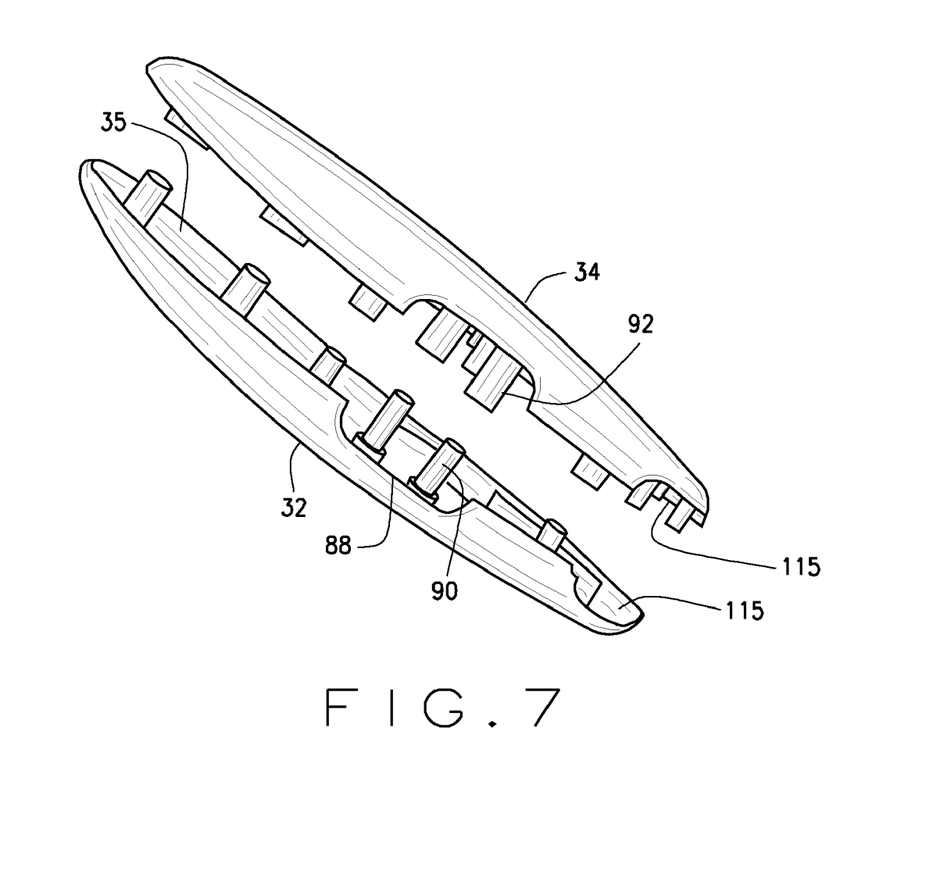
FIG. 7 is an exploded view of first and second casings of the handle.

Referring to FIGS. 6 and 7, the handle 12 provides a means for one-handed operation of the valvulotome device 10 by actuation of the catheter 18. The handle 12 may include a first casing 32 secured to a second casing 34 that collectively define an interior chamber 35 in communication with a slot 88 and an opening 115. An incrementally rotatable thumb wheel 30 extends through the slot 88 and is operatively engaged to the deployable assembly 14 through the catheter 18. Actuation of the catheter 18 is accomplished by rotating the thumb wheel 30 in either a clockwise or counter-clockwise direction that manipulates the catheter 18 in either a distal direction (away from the handle 12) or proximal direction (towards the handle 12) depending on the rotation of the thumb wheel 30.

Figure 8:
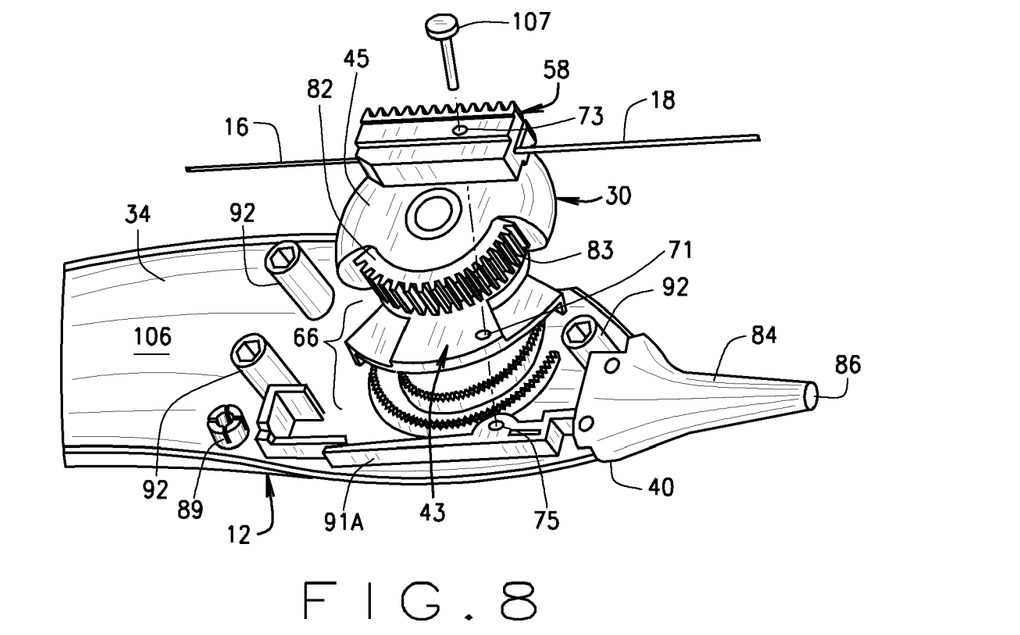
FIG. 8 is a partial exploded view of the handle.
Figure 11:
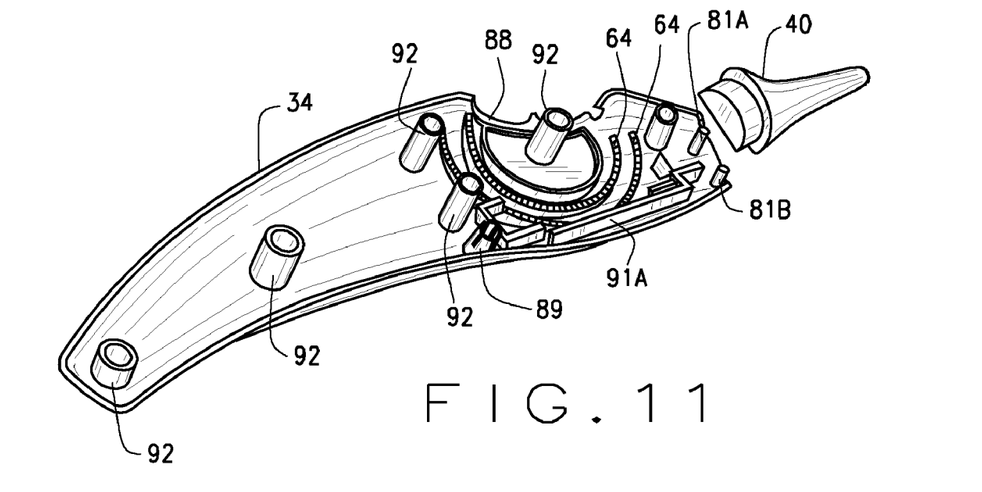
FIG. 11 is a perspective view of the second casing of the handle.

Referring to FIGS. 6, 8 and 11, the handle 12 may include a strain relief 40 having a neck 84 defining an aperture 86. The strain relief 40 functions as a flexible conduit for the passage of the catheter wire 16 and catheter 18 from the opening 115 of the handle 12.

Figure 13:
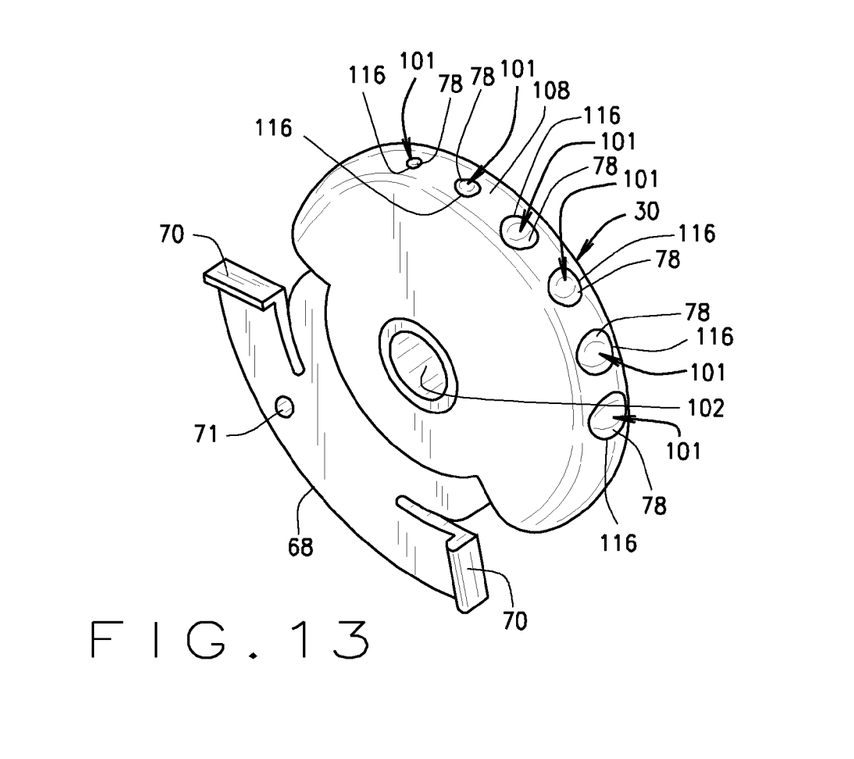
FIG. 13 is a perspective view of the thumb wheel illustrating a directional indicator.
Figure 15:
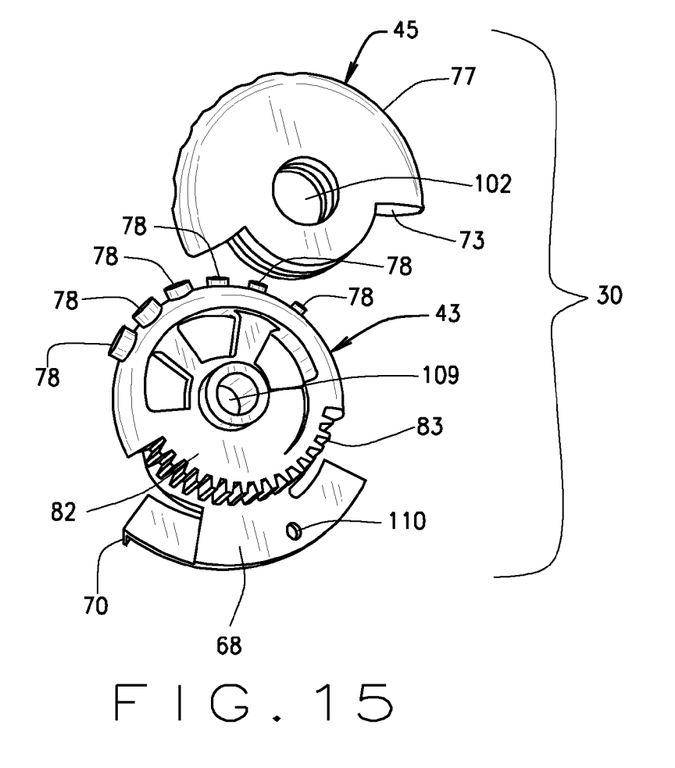
FIG. 15 is an exploded view of the thumb wheel.

Referring to FIGS. 13 and 15, thumb wheel 30 includes a wheel body 45 engaged to a wheel gear 43 disposed inside the interior chamber 35 of handle 12. The wheel body 45 defines a generally disc-shaped body 77 having a rounded peripheral edge 108 defining a plurality of openings 116 in communication with a hollow cavity 73 adapted for engagement with the wheel gear 43. As further shown, the wheel gear 43 defines a plurality of raised indentations 78 adapted to provide a tactile contact surface for rotating the thumb wheel 30. During assembly, the raised indentations 78 are engaged to a respective opening 116 as the wheel gear 43 is secured to the wheel body 45.

When thumb wheel 30 is rotated in one direction, for example in a counter-clockwise direction, the catheter 18 is drawn proximally into the handle 12 which causes the catheter sheath 38 to become incrementally disengaged from the bullet 20, thereby actuating the deployable assembly 14 as the guide fin assembly 22 and blade assembly 24 simultaneously begin to deploy incrementally from the closed position to one or more respective sequential deployment positions. Conversely, rotation of the thumb wheel 30 in the opposite direction, for example in a clockwise direction, causes the catheter 18 to move away from the handle 12 that permits the deployable assembly 14 to incrementally moved from one or more deployment positions to the closed position if desired by the user.

Figure 10:
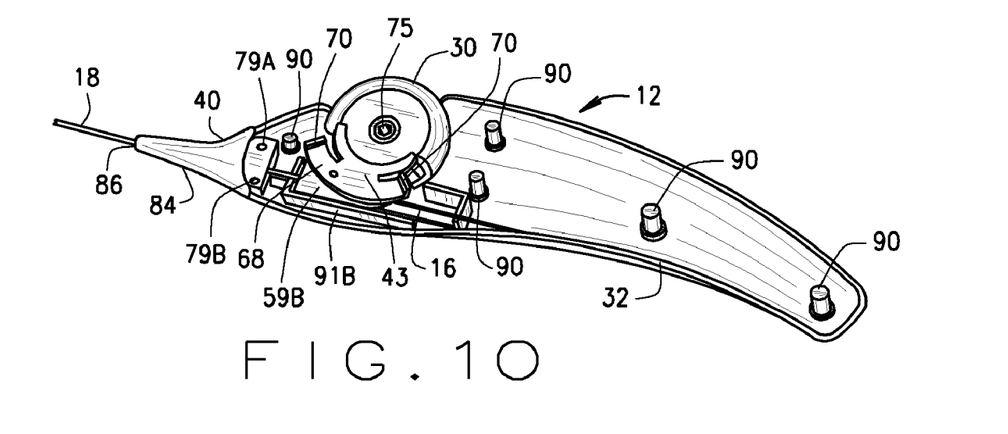
FIG. 10 is a perspective view of the first casing of the handle.

As shown in FIGS. 7, 10 and 11, the first casing 32 may define an interior surface 104 having a plurality of raised knobs 90 which are adapted to engage respective raised receptacles 92 defined along an interior surface 106 of the second casing 34. In one embodiment, the knobs 90 may have a hexagonal-shaped end ends sized and shaped to securely engage a respective receptacle 92 when securing the first casing 32 to the second casing 34 of handle 12, although other types of configurations for the knob 90 and receptacle 92 are contemplated.

Figure 9:
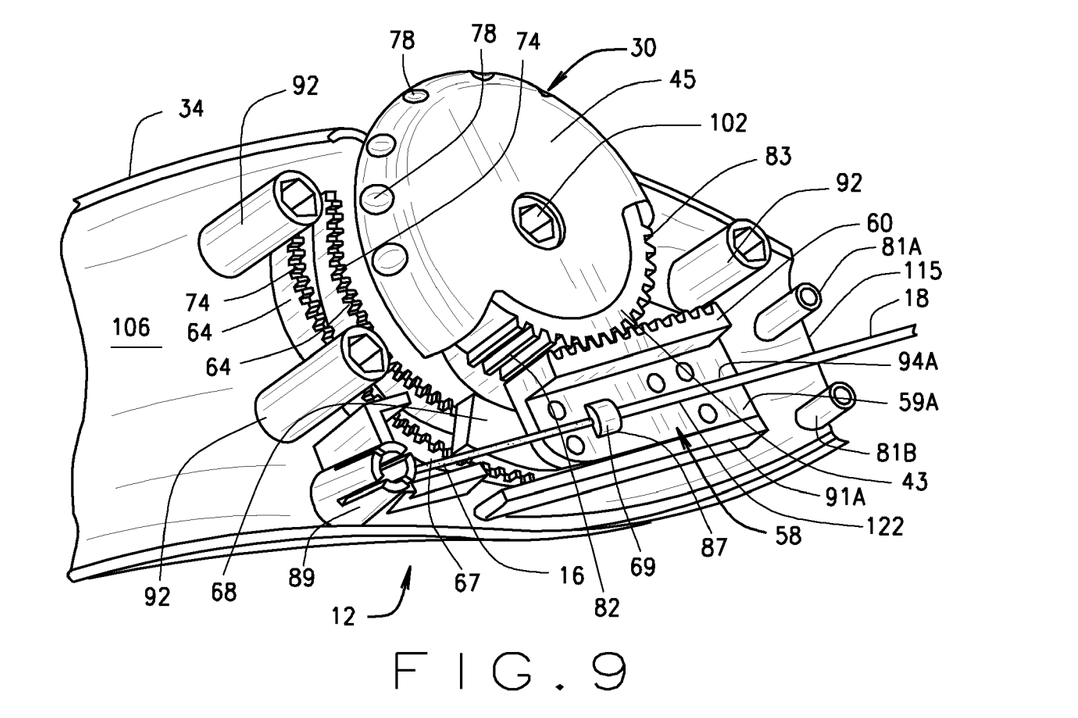
FIG. 9 is an enlarged perspective view of the interior portion of the handle.

Referring to FIGS. 9-11, the thumb wheel 30 defines a center receptacle 102 rotatably engaged to a raised receptacle 92 in order to allow incremental rotation of thumb wheel 30 in either a clockwise or counter-clockwise direction. In addition, the thumb wheel 30 further includes a locking mechanism 66 that provides a means to incrementally rotate the thumb wheel 30 and place the deployable assembly 14 in a particular deployment position or the closed position. The locking mechanism 66 of the thumb wheel 30 may include an arc-shaped arm portion 68 defining laterally extending opposing teeth 70 defined at opposing ends of the arm portion 68. The opposing teeth 70 are adapted to engage and incrementally advance along a pair of arc-shaped tracks 64 defined along the interior surface 106 of second casing 34 as the thumb wheel 30 is being rotated. In one embodiment, each pair of arc-shaped tracks 64 defines a plurality of similarly spaced notches 74 adapted to engage the opposing teeth 70 of the arm portion 68. As such, the locking mechanism 66 provides a tactile indication of incremental movement of the thumb wheel 30 as the opposing teeth 70 of the arm portion 68 advance along the notches 74 of tracks 64 as the thumb wheel 30 is being rotated.

As noted above, the engagement of the opposing teeth 70 with notches 74 provides the tactile indication of incremental movement of the thumb wheel 30 as the opposing teeth are advanced to the next notch 74 along tracks 64. Accordingly, the locking mechanism 66 allows the thumb wheel 30 to be rotated into a specific incremental position as opposing teeth 70 ride along the arc-shaped tracks 64 that corresponds to the closed position or to one or more deployment positions for the deployable assembly 14.

Figure 12:
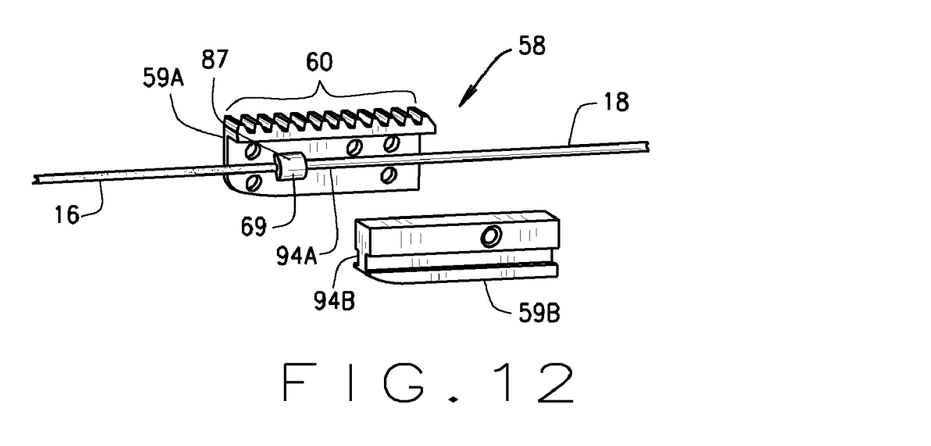
FIG. 12 is an isolated exploded view of a linear rack engaged to the catheter and a catheter wire.

Referring to FIG. 8, the wheel gear 43 may include a pinion gear portion 82 defining a plurality of pinion gear teeth 83 adapted to operatively engage a linear rack 58 operatively disposed along first and second tracks 91A and 91B (FIG. 10) defined by the interior surfaces 104 and 106 of first and second casings 32, 34, respectively. As shown in FIG. 12, the linear rack 58 includes a two-part rack body 59A and 59B for providing a means of manipulating the catheter 18 and actuating the deployable assembly 14 by rotation of the thumb wheel 30. As further shown, rack body 59A defines a plurality of linear gear teeth 60 adapted to engage pinion gear teeth 83 of the wheel gear 43 such that rotation of thumb wheel 30 causes the linear rack 58 to move in a linear fashion in either a proximal or distal direction along tracks 91A and 91B as the arm portion 68 incrementally engages tracks 64. In one embodiment, rotation of the thumb wheel 30 in a clockwise direction causes the linear rack 58 to move in a linearly proximal direction A toward the proximal portion of the handle 12 along tracks 91A and 91B as illustrated by the sequence shown in FIGS. 16A, 16B and 16C, while rotation of the thumb wheel 30 in a counter-clockwise direction causes the linear rack 58 to move in a linearly opposite distal direction B toward the distal portion of the handle 12.

Rack body 59A may define a channel 94A while rack body 59B may define a corresponding channel 94B such that a conduit is collectively defined between channels 94A and 94B that communicate with an anchor portion 87 also collectively defined by rack body 59A and 59B. The catheter 18 includes a proximal end 122 which defines a flange 96 that is adapted to be securely engaged within the anchor portion 87. As such, the linear movement of the linear rack 58 along tracks 91A and 91B by rotation of thumb wheel 30 causes the catheter 18 to be concurrently moved in the same linear direction (proximal or distal) as the linear rack 58 in order to either disengage the catheter sheath 38 from the bullet 20 when actuating the deployable assembly 14 from the closed position to one or more deployment positions or sequentially back through one or more attained deployment positions to the closed position.

Figure 16A:
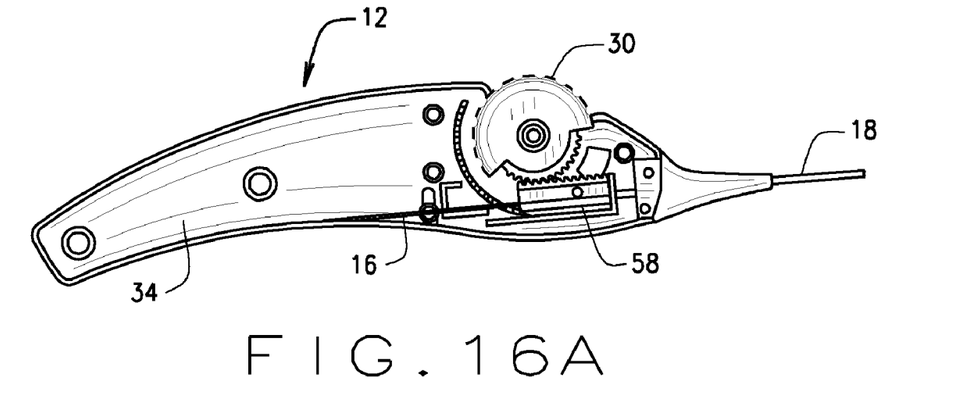
FIGS. 16A-16C are cross-sectional side views that illustrate a sequence of operating the handle.
Figure 16B:
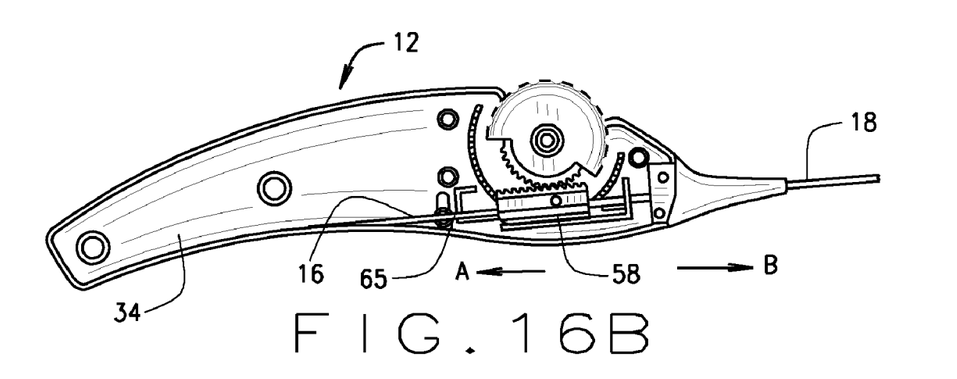
Figure 16C:
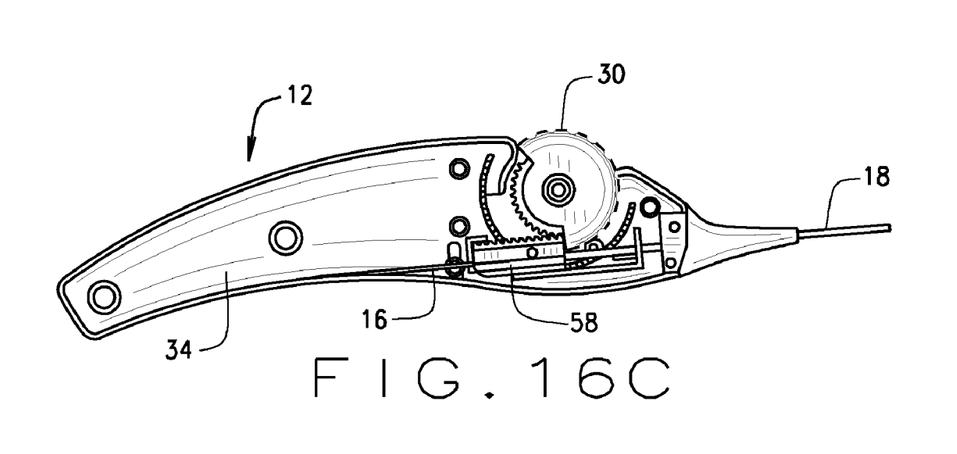

Referring to FIGS. 16A-16C, when the linear rack 58 is incrementally advanced linearly from a maximum distal position in the proximal direction A the deployable assembly 14 is moved from the closed position (FIG. 16A) to one or more sequential deployment positions (FIG. 16B representing one particular deployment position) until the linear rack 58 reaches the maximum proximal position (FIG. 16C). Movement of the linear rack 58 in the distal direction B causes the linear rack 58 to be moved back from the maximum proximal position (FIG. 16C) towards the maximum distal position (FIG. 16A) such that the catheter sheath 38 engages the bullet 20 and places the deployable assembly 14 in the closed position.

As noted above, the catheter wire 16 is encased inside the handle 12 and extends from the flange 69 of the catheter 18 with the proximal end 65 of the catheter wire 16 being secured to a set screw 62 engaged to a set screw base 89 defined along second casing 34. The set screw 62 provides a means for calibrating the catheter wire 16 by rotating the set screw 62 in order to shorten or lengthen the catheter wire 16 relative to the handle 12. In addition, an alignment screw 107 may be adapted to be inserted through alignment holes 71, 73 and 75 defined through the wheel gear 43, linear rack 58, and second casing 34, respectively, during assembly of the handle 12.

Figure 14:
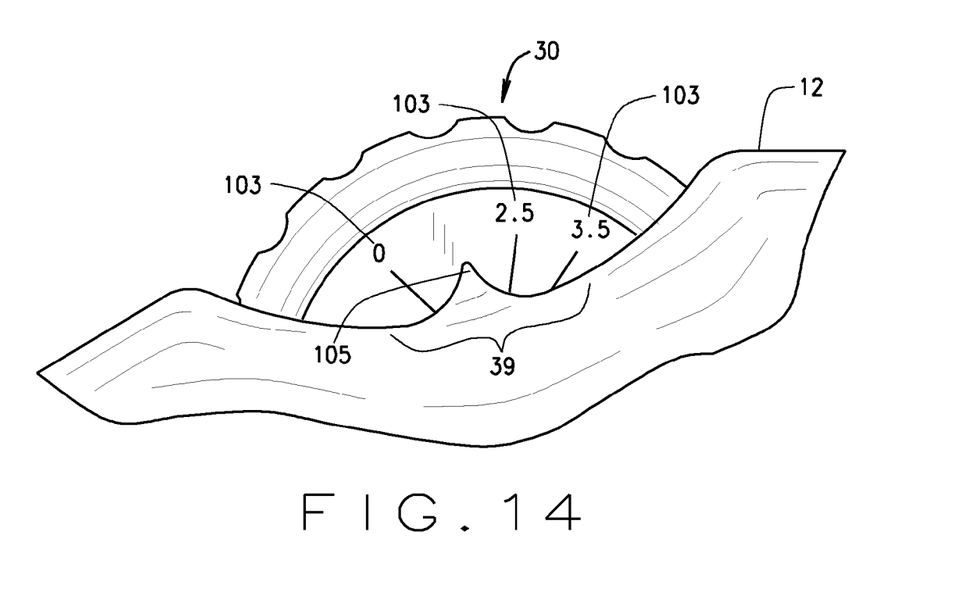
FIG. 14 is a side view of the thumb wheel partially disposed inside the handle illustrating a visual indicator of the deployment position of the valvulotome.

Referring to FIGS. 13 and 14, the thumb wheel 30 also provides a means for visually determining the particular deployment position of the deployable assembly 14 as well as a means for determining the rotational direction (clockwise or counter-clockwise) of the thumb wheel 30. As noted above, the thumb wheel 30 defines a plurality of raised indentations 78 that provide a tactile gripping surface for assisting the user to rotate the thumb wheel 30 when operating the valvulotome device 10. In addition, markers 101 may be included on each indentation 78 for providing a visual indication of the rotational direction of the thumb wheel 30 during operation. In one embodiment, markers 101 may be provided along successive indentations 78 with each successive marker 101 having a larger shape than the previous marker 101. In one embodiment, this arrangement of sequentially larger sized markers 101 along successive indentations 78 provides a visual indication to the user as to a rotational direction, i.e. clockwise or counter-clockwise, that the thumb wheel 30 is being rotated. In another embodiment, successively larger markers 101 in one direction may indicate a clockwise direction, while the same successively smaller markers 101 in the opposite direction may indicate a counter-clockwise direction be taken by the rotating thumb wheel 30.

Figure 14A:
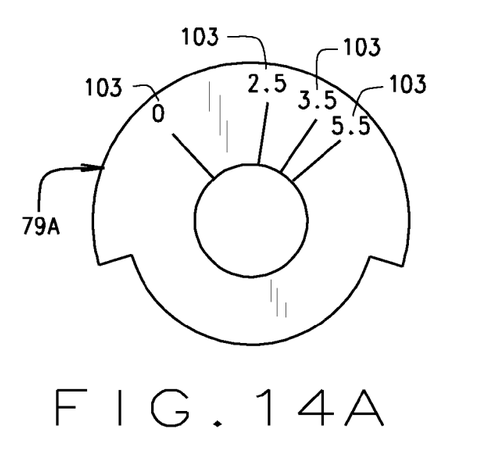
FIGS. 14A and 14B are respective side views of opposing decals used with the visual indicator of FIG. 14.
Figure 14B:
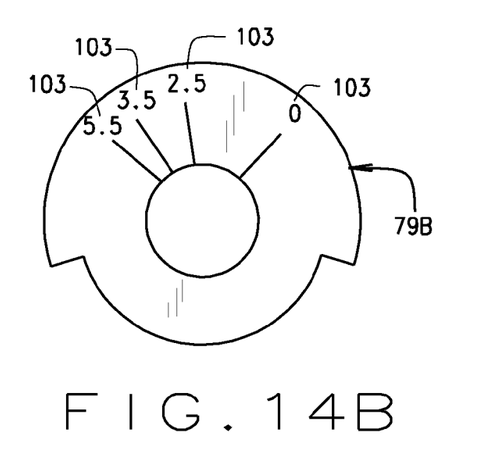
Figures 17, 17A, 18, 18A, 19, 19A, 20, 20A, 21:
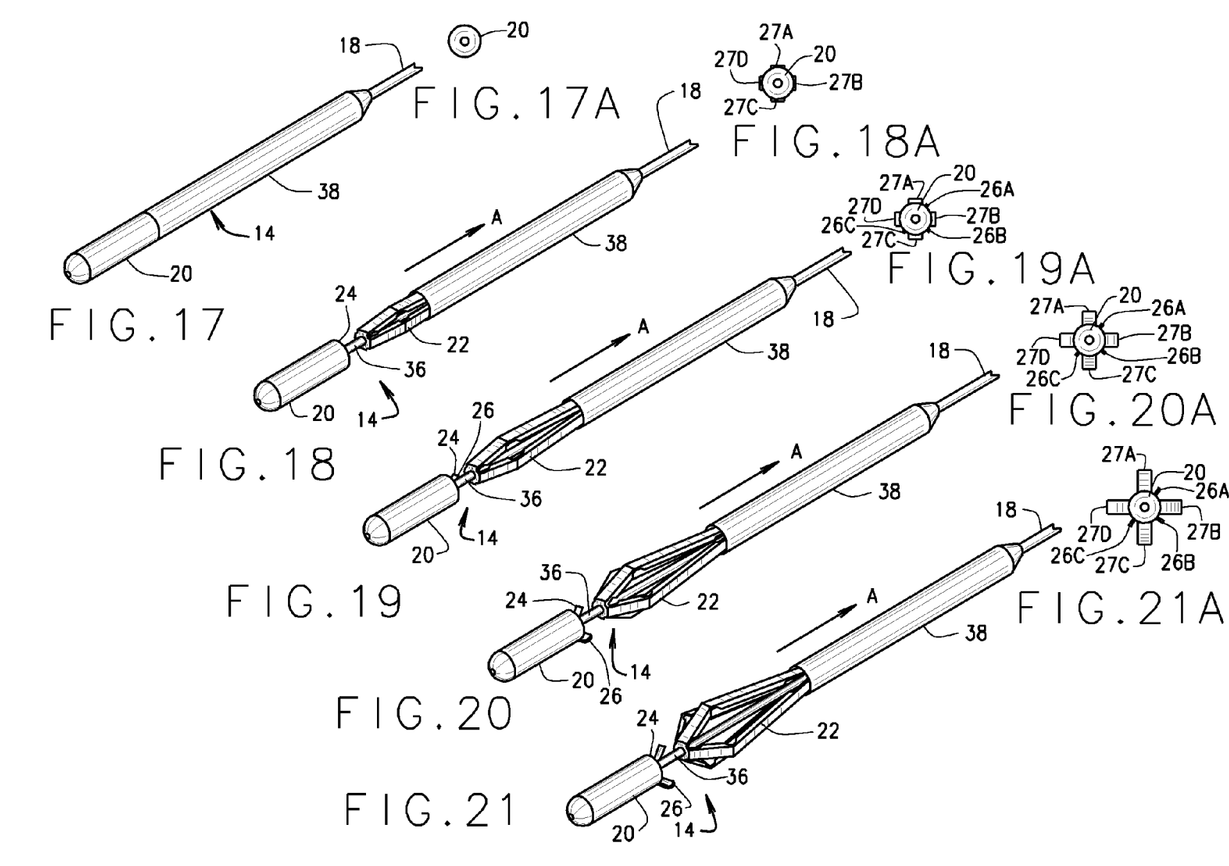

Referring to FIG. 18, the thumb wheel 30 may include a visual indicator 39 that provides a visual indication as to the specific deployment position of the deployable assembly 14. The visual indicator 39 includes a series of numbers 103 that correspond to the outer diameter of the guide fins 27 for particular deployment position of the deployable assembly 14. In one embodiment, a number 103 may indicate that the deployable assembly is in the closed position or "zero" position, while successive numbers 103 may indicate the respective outer diameter of a particular deployment position of the guide fin assembly 22, for example 2.5 mm, 3.5 mm, 4.5 mm and 5.5 mm. However, other numbers 103 may indicate other values for the outer diameter of a particular deployment position for the guide fin assembly 22. As shown, the opposing sides of slot 88 may define a pointed indicator 105 that visually points to the particular outer diameter of the guide fin assembly 22 that the thumb wheel 30 is set at that particular deployment position. Referring to FIGS. 14A and 14B, a left decal 79A and a right decal 79B may be applied to opposing sides of thumb wheel 30. Each decal 14A and 14B includes numbers 103 corresponding to a particular outer diameter of the guide fin assembly 26 at a specific deployment position assumed by the deployable assembly 14.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A valvulotome device (10) comprising:
   a handle (12) having a thumb wheel (30), the thumb wheel (30) being operatively associated with a catheter (18) that encloses a catheter wire (16), and
   a deployable assembly (14) operatively engaged to the thumb wheel (30) through the catheter (18) and catheter wire (16), the deployable assembly (14) including a blade assembly (24) having a plurality of cutting blades (26) and a guide fin assembly (22) having a plurality of guide fins (27) with a connection tube (36) interposed between the blade assembly (14) and the guide fin assembly (22); wherein the deployable assembly (14) is deployable from a closed position to one or more deployment positions upon actuation of the catheter (18) by the handle (12) such that the blade assembly (24) and the guide fin assembly (22) incrementally and simultaneously deploy to the one or more deployment positions by deployment of the plurality of cutting blades (26) and plurality of guide fins (27) to a respective outer diameter for each of said one or more deployment positions, wherein said catheter (18) defines a proximal end (122) operatively associated with said thumb wheel (30) and a distal end (120) that communicates with a hollow catheter sheath (38), said catheter sheath (38) being engaged to a hollow bullet (20) for collectively containing said deployable assembly (14) in said closed position, wherein said handle (12) includes a first casing (32) engaged to a second casing (34), said first casing (32) and said second casing (34) collectively defining a chamber (35) in communication with a slot (88) and an opening (115), wherein said first casing (32) defines a first track (91A) and said second casing (34) defines a second track (91B), said first casing (32) defining a pair of arcuate tracks (64) wherein said handle (12) further includes a linear rack (58), said linear rack (58) being adapted for linear movement along said first and second tracks, said linear rack (58) defining a first rack body (59A) having a channel (94A) and a second rack body (59B) having a channel (94B) that collectively define a conduit and an anchor portion (87) adapted to engage said catheter (18), said first rack body (59A) defining a plurality of linear gear teeth (60) wherein said catheter (18) includes a flange (69) adapted to be disposed inside said anchor portion (87) of said linear rack, wherein linear movement of said linear rack (58) causes movement of said catheter (18) in either a distal direction (B) or proximal direction (A) such that movement in the distal direction (B) causes the deployable assembly (14) to deploy from said closed position to said one or more sequential deployment positions wherein said thumb wheel (30) includes a wheel gear (43) and a wheel body (45), said wheel body (45) defining a rounded peripheral edge (108) having a plurality of openings (116) in communication with a cavity (73), said wheel gear (43) having a pinion gear portion (82) defining a plurality of pinion gear teeth (83) adapted to engage said linear gear teeth (60) of said linear rack (58), said wheel gear (43) further including an arm portion (68) defining a pair of opposing teeth (70), said opposing teeth (70) being adapted to incrementally engage said pair of arcuate tracks (64) when said thumb wheel (30) is rotated wherein said handle includes raised protrusions, each of said raised protrusions (78) includes a respective marker (101), each respective marker (101) providing a visual indication as to the rotational direction of said thumb wheel (30) wherein rotation of said thumb wheel (30) in one direction causes the linear rack (58) to move said catheter (18) in said proximal direction (A) and rotation of said thumb wheel (30) in an opposite direction causes the liner track (58) to move said catheter (18) in said distal direction (B).

2. The valvulotome device (10) according to claim 1, wherein said respective outer diameter of said guide fins (27) is larger than said respective outer diameter of said cutting blades (26) at each of said one or more deployment positions.

3. The valvulotome device (10) according to claim 1, wherein said guide fins (27) and said cutting blades (26) having no outer diameter in relation to the catheter sheath.

4. The valvulotome device (10) according to claim 1, wherein said thumb wheel (30) is rotatably disposed within said slot (88).

5. The valvulotome device (10) according to claim 1, further including a strain relief (40) engaged to said opening (115) of said handle (12), said strain relief (40) having a neck (84) defining an aperture (86) adapted to permit said catheter (18) to be inserted therethrough.

6. The valvulotome device (10) according to claim 1, wherein said hollow catheter sheath (38) becomes disengaged from said hollow bullet (20) when said deployable assembly (14) deploys to said one or more deployment positions.

7. The valvulotome device (10) according to claim 6, wherein said hollow catheter sheath (38) becomes engaged to said hollow bullet (20) when said catheter (18) is moved away from said handle (12), while the catheter sheath (38) becomes disengaged from said hollow bullet (20) when said catheter (18) is moved toward said handle (12).

8. The valvulotome device (10) according to claim 1, wherein said hollow catheter sheath (38) becomes disengaged or engaged to said hollow bullet (20) when said catheter (18) is actuated by said handle (12).

9. The valvulotome device (10) according to claim 1, wherein said slot (88) defines a pointed indicator (105) and said thumb wheel (30) includes a visual indicator (39) having a series of numbers (103) corresponding to the outer diameter for a particular deployment position taken by said guide fin assembly (22), wherein said pointed indicator (105) points to one of said series of numbers (103) to indicate said particular deployment position of said deployable assembly (14).

10. The valvulotome device (10) according to claim 1, wherein each of said plurality of guide fins (27) includes a long portion (53) and a short portion (55) with a bendable portion (57) interposed between said long portion (53) and said short portion (55) for permitting each of said plurality of guide fins (27) to expand to said one or more deployment positions.

11. The valvulotome device (10) according to claim 1, wherein each of said plurality of guide fins (27) has the same outer diameter and each of said plurality of cutting blades (26) has the same outer diameter.

12. The valvulotome device (10) according to claim 1, wherein said catheter wire (16) maintains a fixed spatial relationship between said handle (12) and said deployable assembly (14).

* * * * *